United States Patent [19]

Michaels

[11] 4,107,328

[45] Aug. 15, 1978

[54] ANTIMICROBIAL COMPOSITIONS AND METHODS FOR UTILIZING THE SAME EMPLOYING MIXTURES OF AMINES

[76] Inventor: Edwin B. Michaels, Gregory Ct., East Norwalk, Conn. 06855

[21] Appl. No.: 800,898

[22] Filed: May 26, 1977

Related U.S. Application Data

[63] Continuation-in-part of Ser. No. 641,727, Dec. 18, 1975, abandoned, which is a continuation-in-part of Ser. No. 564,454, Apr. 2, 1975, abandoned.

[51] Int. Cl.$^2$ .............................................. A01N 9/20
[52] U.S. Cl. .................................... 424/316; 424/320; 424/325; 252/107
[58] Field of Search ................................ 424/316, 329

[56] References Cited

U.S. PATENT DOCUMENTS 3,484,523  12/1969  Findlan et al. ....................... 424/329

OTHER PUBLICATIONS

Kirk–Othmer Encyc. of Chem. Tech., 2nd Ed., vol. 19 (1969) pp. 555–566, 575–577.

*Primary Examiner*—V. D. Turner

[57] ABSTRACT

There are provided antimicrobial compositions of the low toxicity having enhanced activity against gram positive and gram negative bacteria as well as fungi or protozoa and consists essentially of:
(a) an alkyl-N-betaine in amounts up to 40 parts, by weight,
(b) an alkyl-N,N-dimethylamine oxide, an alkyl-N,N-dihydroxy-ethylamine oxide, or an acylamido t-amine oxide in amounts up to 40 parts, by weight, and
(c) a protonating agent, such as hydrochloric acid, acetic acid or citric acid in an amount sufficient to adjust the pH of the overall composition to from about 4.0 to about 5.5.

The composition exhibits skin degerming, cleansing, and deodorizing properties and, particularly, its use exhibits long term inhibition of body odor.

16 Claims, No Drawings

ANTIMICROBIAL COMPOSITIONS AND METHODS FOR UTILIZING THE SAME EMPLOYING MIXTURES OF AMINES

This application is a continuation-in-part of my copending application, Ser. No. 641,727, filed on Dec. 18, 1975, now abandoned, which in turn is a continuation-in-part of my application Ser. No. 564,454, filed on Apr. 2, 1975, now abandoned.

The present invention relates to antimicrobial compositions of enhanced efficacy and safety. More particularly, the invention relates to antimicrobial compositions having low toxicity and broad spectrum, antimicrobial activity consisting essentially of certain surfactants which individually have limited antimicrobial use. Still more particularly, the invention is concerned with antimicrobial compositions of enhanced gram positive and gram negative activity consisting essentially of in admixture:

(a) an alkyl-N-betaine from 0.1 to 40.0 parts, by weight, (b) an alkyl-N,N-dimethylamine oxide, an acrylamido t-amine oxide, or an alkyl-N,N-dihydroxyethyl amine oxide from 0.1 to 40.0 parts, by weight, and (c) a protonating agent, such as hydrochloric acid, acetic acid or citric acid, in an amount sufficient to adjust the pH of the overall composition in the range from about 4.0 to about 5.5.

The compositions of the present invention, useful as topical germicides, exhibit sustained periods of antimicrobial activity, particularly in the control of body odor.

It is known that a method for the control of body odor is to thoroughly wash the body with soap. However, the microbial flora of the skin are so prolific that distinctive malodors tend to return within several hours after washing. To provide longer periods of protection, there have been developed compositions which contain either an astringent, such as aluminum chlorohydrate, that inhibits apocrine and eccrine gland secretions or an antimicrobial agent, such as hexachlorophene or trichlorocarbanilamide. Unfortunately, an astringent composition has limited value, since it has little or no control of microbial decomposition of debris and uncontrolled secretions and, where there is control of secretions by antimicrobials, such use suffers from a severe shortened period to obtain effective control of body odor. Nonetheless, such latter antimicrobial compositions of shortened time effectiveness have enjoyed widespread use. In this connection, however, there have been recent investigations into topical and systemic toxicity of the hereinabove named germicides. These investigations have led to severe restrictions, for instance, on the utilization of hexachlorophene and the recognition of the dangers of other germicides. Further, astringents have only limited utility usually due to the harsh or corrosive action on skin, particularly, on people who have sensitive skin. If a safe and effective antimicrobial composition of low toxicity could be provided which would inhibit the development of body odor for relatively long periods of time for at least twenty-four hours, or longer, such a composition would satisfy a well recognized need in the art.

It is a principal object of the invention to provide a composition of enhanced efficacy and safety which possesses broad spectrum, antimicrobial activity in combating body odor as well as a variety of topical infections. It is a further object of the invention to provide an antimicrobial composition comprising at least an alkyl-N-betaine surfactant and an alkyl-N,N-dimethylamine oxide, an acylamido t-amine oxide, or an alkyl-N,N-dihydroxyethylamine oxide, adjusted to a pH of about 4.0 to about 5.5 so as to control gram positive bacteria, gram negative bacteria, fungi and protozoa when topically applied. Other objects and advantages will become apparent from a consideration of the ensuing description.

According to the invention, there are provided antimicrobial compositions consisting essentially of a mixture of (a) an alkyl-N-betaine and (b) an alkyl-N,N-dimethylamine oxide, or an alkyl-N,N-dihydroxyethylamine oxide, or an acylamido t-amine oxide. The compositions are prepared by admixing the same at a temperature ranging from about 25° to 80° C in a substantially aqueous or non-aqueous environment and adjusted to a pH of about 4.0 to about 5.5 to provide a substantially uniform homogeneous composition having both enhanced broad spectrum antimicrobial activity and low toxicity.

In general, a first component, namely, alkyl-N-betaine surfactant employed as a non-ionizing zwitter-ion can be written as:

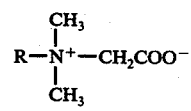

where R is a higher alkyl having from 10 to 18 carbon atoms. Illustrative of such alkyl-N-betaine is coco-N-betaine, cetyl-N-betaine, stearyl-N-betaine, isostearyl-N-betaine, or oleyl-N-betaine, or mixtures of the same.

A second component, namely, the (1) alkyl-N,N-dimethylamine oxide, (2) alkyl-N,N-dihydroxyethylamine oxide, or (3) acylamido t-amine oxide component of the aforementioned mixture, respectively, has the structure:

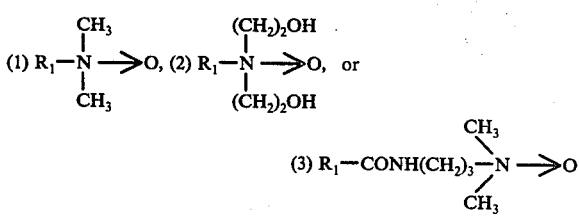

where $R_1$ in each is a higher alkyl from 10 to 18 carbon atoms, as for instance, a radical such as decyl, undecyl, lauryl, tridecyl, myristyl, cetyl, stearyl, isostearyl, oleyl or mixtures of the same. Exemplary of the latter amine oxides are: decyl-N,N-dimethylamine oxide, lauryl-N,N-dimethylamine oxide, stearyl-N,N-dimethylamine oxide, oleyl-N,N-dimethylamine oxide, cocoamido-trimethylene-N,N-dimethylamine oxide, stearylamido-trimethylene-N,N-dimethylamine oxide, decyl-N,N-dihydroxyethylamine oxide, lauryl-N,N-dihydroxyethylamine oxide, coco-N,N-dihydroxyethylamine oxide, stearyl-N,N-dihydroxyethylamine oxide, oleyl-N,N-dihydroxyethylamine oxide, and mixtures of the same.

To attain the desired antimicrobial effects achieved herein, it is essential to provide a protonating agent to supply the required pH to the overall composition. Exemplary of the latter agents are, for instance, any suitable organic or inorganic acid, such as hydrochloric acid, phosphoric acid, sulfuric acid, citric acid, acetic acid, nicotinic acid, and the like. A critical operating pH for the overall composition ranges from 4.0 to 5.5 and, preferably, from about 4.7 to 5.2. The pH of an aqueous solution comprising the above enumerated components of the invention is determined by employing 0.5%, by weight, of the two active components at a glass electrode to precisely define the acidity of the composition. In general, it is found that at a pH below 4.0, the action of the mixture of amine oxide and alkyl betaine is so harsh or corrosive on skin that one cannot safely employ the same for topical applications. Further, at a pH below 4.0, there is noted a marked decrease in activity against gram positive bacteria. At a pH above 5.5, the antimicrobial effect is also markedly decreased and, hence, is substantially ineffective, particularly with respect to gram negative organisms.

In practice, each of the components of the overall composition ranges widely from 0.1 part to 40.0 parts and, preferably, from 1 to 20 parts, all by weight. There is added to the mixture a polar inert solvent, such as water or a lower monohydric aliphatic alcohol, water being preferred, for a total of at least 100 parts. Where water is employed small amounts of a lower alkyl alcohol, such as ethanol or propanol, may also be added thereto to provide ease in formulation. The pH of the total composition is then adjusted to the requisite pH by adding a suitable aforementioned inorganic or organic acid thereto. The composition can be employed as a solution, as a spray in a suitable propellant, such as an aerosol spray utilizing commercially available "Freon" fluorocarbon, butane or equivalent propellant. Alternatively, the composition can be prepared as a solid cake when admixed with suitable fillers.

Advantageously, the compositions of the present invention possess an extremely low toxicity, exhibiting at use concentration an $LD_{50}$ in Swiss-Webster mice having a value greater than fifteen grams per kilogram by oral administration which is considered to be non-toxic. Further, there are observed a lack of primary irritation to the skin and less eye irritation as compared with ordinary soap.

In general, the compositions of the present invention can be used to treat a variety of microbial infections in a wide variety of concentrations. For instance, when bactericidally effective amounts containing the combined components ranging from 0.1 to 40 parts, by weight, and preferably from 1 to 20 parts, by weight, of the active components per 100 parts, by weight, of the overall mixture, are applied to infected or uninfected wounds, including either pyogenic or burn wounds, rapid healing is observed. The compositions are capable of relieving ear infections where solutions of the compositions of the invention are employed as an ear douche. Dandruff, crotch itch, athlete's foot, and acne caused by mild microbial infections are capable of being eliminated. Significantly, the compositions of the present invention when preferably employed as a general personal body wash, body odors particularly in the axillary, anal and genital areas are inhibited for periods in excess of twenty-four hours, and longer. Hence, the compositions are capable of use in a wide variety of preparations involving the cosmetic, medical and veterinary areas.

The microorganisms causing the hereinabove described conditions are generically bacteria, fungi or protozoa. Illustrative bacteria are Staphylococcus aureus, Staphylococcus epidermidis, Proteus vulgaris, Escherichia coli, Bacillus subtilis, Streptococcus pyogenes, Salmonella tyhimirium, Pseudomona aerriginosa, Klebsiela pneumoniae and Shigella flexniri. Exemplary fungi include Candida albicans, Trichophyton mentagrophytes and Saccharomyces cerevisiae. Typical protozoa species, such as Trychomonas vaginalis and Entamaeba histolytica, are also adversely affected when subjected to the compositions of the present invention.

In order to facilitate a further understanding of the invention, the following examples are presented primarily for purposes of illustrating certain more specific details thereof. The invention is not to be deemed as limited thereby except as defined in the claims. Unless otherwise noted, all parts and percentages are by weight.

EXAMPLE 1

In this in vivo example, several compositions are employed and used as a body wash. These compositions are set forth in the table below.

Thirteen panels each consisting of five men and five women as subjects are selected and supplied with samples of the compositions as defined below and a soap control. After 24 hours have elapsed since the panel members' last washing, each is instructed to wash, noting particularly the axillary odor before and after washing.

The bacteria noted on the skin of the panel members in this example which are among those reported responsible for body odor are Staphylococcus aureus, Staphlococcus epidermidis, Proteus vulgaris and Escherichia coli. The panel members are then monitored and examined during the next 24 hours, and longer, for the time span when typical body odors develop. These times are then noted and recorded in Table 1 below.

TABLE I

| Panel No. | Composition used by each panelist | Average Elapsed Time Body Odor is Detected (hours) |
|---|---|---|
| 1. | Coco-N-betaine(6%) plus cocoamido-N, N-dimethylamine oxide(6%) in distilled water, citric acid(0.55%) in distilled water at a pH=5. | 72 |
| 2. | Cetyl-N-betaine-4%, plus 70/30 myristyl/palmitic-N,N-dimethylamine oxide-6% in distilled water, adjusted to pH=5. with acetic acid. | 60 |
| 3. | Cetyl-N-betaine-6% plus Oleyl-N,N-dimethylamine oxide-6% in distilled water, adjusted to pH=5.5 with citric acid. | 54 |
| 4. | 70/30 Myristyl/palmitic-N,N-dihydroxyethylamine oxide-6% + coco-N-betaine-6% in distilled water, adjusted to a pH=5.2 with citric acid. | 96 |

TABLE I-continued

| Panel No. | Composition used by each panelist | Average Elapsed Time Body Odor is Detected (hours) |
|---|---|---|
| 5. | Cocoamido-N,N-dimethylamine oxide(12%) in distilled water-pH adjusted to 7. | 8 |
| 6. | Cocoamido-N,N-dimethylamine oxide(12%) in distilled water - pH adjusted to 5.4 with citric acid. | 10 |
| 7. | Coco-N-betaine(12%) in distilled water - pH adjusted to 6.2. | 12 |
| 8. | Coco-N-betaine(12%) in distilled water - pH adjusted to 5.4 with citric acid. | 12 |
| 9. | Coco-N-betaine(6%)+coco-N,N-dimethylamine oxide(6%) in distilled water adjusted to pH of 6.4 with citric acid. | 12 |
| 10. | 70/30 Myristyl/palmitic-N,N-dimethylamine oxide(12%) in distilled water-pH adjusted to 5.5 with citric acid. | 12 |
| 11. | Decyl-N,N-dimethylamine oxide(12%) in distilled water-pH adjusted to 5.2 with acetic acid. | 8 |
| 12. | 70/30 Myristyl/palmitic-N,N-dimethylamine oxide(6%) + lauryl-N,N-dimethylamine oxide-(6%) in distilled water, adjusted to a pH of 5.2 with citric acid. | 10 |
| 13. | Ivory Soap | 6 |

In the above table, it can be clearly seen that the two component compositions of the present invention at the critically adjusted pH range cause a marked improvement in body odor inhibition as compared to a one component system or even a two component system at a pH above 5.5. Compositions adjusted to a pH below 4 could not be employed, since they are too corrosive and harsh.

EXAMPLE 2

The relationship between antimicrobial activity for the bacteria enumerated above and control of body odor is determinded by subjecting some panel members of Example 1 to washing tests employing typical compositions of Example 1. There are obtained the density of microbes comprising Staphylococcus aureus, Staphylococcus epidermidis, Proteus vulgaris, and Escherichia coli in the axillary area of each panelist by using a 3 inch in diameter Rodac plate comprising Tryptose soy agar with Tween ® 80 and lecithin to neutralize any residual test composition. The panelist presses the plate for 30 seconds to the axillary area of the armpit. The plates are then incubated at 37° C for 24 hours and the number of microorganisms as colonies are counted. The density of the colonies per square inch is next calculated.

The data obtained are noted in the table below and are the average values of the subjects treated.

TABLE II

| Composition of Example 1 | No. of colonies 0 hours after washing | No. of colonies 12 hours after washing | No. of colonies 24 hours after washing | No. of colonies 48 hours after washing |
|---|---|---|---|---|
| 1 | 400 | 900 | 1300 | 2000 |
| 2 | 300 | 350 | 1100 | 1000 |
| 5 | 1000 | 2300 | TNC* | TNC* |
| 6 | 1200 | 2500 | TNC | TNC |
| 7 | 1000 | 2350 | TNC | TNC |
| 8 | 1100 | 2450 | TNC | TNC |
| 9 | 1200 | 2500 | TNC | TNC |

*TNC means too numerous to count - The density is greater than 3000 colonies per square inch.

EXAMPLE 3

There are admixed in a suitable vessel at 40° C stearyl-N-betaine (6.25 gm.), coco-N,N-dimethylamine oxide (13 gm.), citric acid (4.5 gm.) and 125 gm. of distilled water. The pH of the mixture when diluted to 0.5% actives is equal to 5.0.

The mixture is tested as a body shampoo on a panel of five males and five female adults and after 60 hours subsequent to washing, the panel reports no evidence of body odor in the axillary areas.

EXAMPLE 4

A mixture of stearyl-N-betaine (6.5 gms.), coco-N,N-dimethylamine oxide (13 gms.), acetic acid (4.5 gms.), and 66 gms. of water, formed at 50° C and having a pH on dilution is equal to 5.1, is employed as a body wash as in Example 3 above. Body odor is absent after 72 hours.

Substituting hydrochloric acid for acetic acid in the above mixture, similar results are noted.

EXAMPLE 5

There are admixed cetyl-N-betaine (2.5 gms.), myristyl-N,N-dimethylamine oxide (5.5 gms.), citric acid (2.0 gms.), and 87 gms. of water. The mixture is heated to 60° C and the pH determined on dilution is 5.5.

As in Example 4 above, the mixture is used as a body wash to determine axillary and pubic body odors. After 72 hours subsequent to washing, no body odor is detected. Moreover, panel members with dandruff report complete control of dandruff after 2 days' use when washing once each day with the above composition.

EXAMPLE 6

A mixture of lauryl-N-betaine (5.2 gms.), 70/30 myristyl/palmitic-N,N-dimethylamine oxide mixture (5.5 gms.) citric acid (0.7 gms.) and water (108 gms.) is heated to 35° C. The pH of the diluted solution is 5.4 and is used as a body wash. No body odor is detected for 72 hours after washing.

EXAMPLE 7

There are added at 30° C 6.2 gms. of coco-N-betaine, 6.2 gms. of 70/30 myristyl/palmitic-N,N-dimethylamine oxide, 5. gms. of isopropanol, 0.7 gm. of citric acid, and 92 gms. of water. Upon dilution, the pH measured equals 5.5.

The mixture is used as a body shampoo and controls body odor for 48 hours after washing in all panel members.

EXAMPLE 8

There are admixed at 75° C in a suitable vessel 3.25 gms. of cetyl-N-betaine, 3.25 gms. of coco-N-betaine, 6.5 gms. of 70/30 myristyl/palmitic-N,N-dimethylamine oxide, 1 gm. of isopropanol, 1.2 gms. of citric acid, and 84.8, gms. of water. There is obtained a solution having a pH=5.

The composition, when used normally as a body wash, controls odor for more than 96 hours after washing.

EXAMPLE 9

This example illustrates the formulation of a solid composition. A solid cake is prepared by blending 32 gms. of stearyl-N-betaine, 32 gms. of myristyl/palmitic-N,N-dimethylamine oxide, 20 gms. of isopropanol, 40 gms. of water, 6.3 gms. of citric acid and 50 grams of Carbowax® polyethylene glycol having a molecular weight of 10,000. This mixture is vigorously stirred and heated to a temperature of 80° C. Resultant composition is then dried by evaporation and cooled. There is recovered a waxy solid product having a pH equal to 5.0 at a 0.5% aqueous concentration.

The solid composition is employed as solid detergent for washing and controls body odor for 48 hours after washing.

EXAMPLE 10

In this example there is prepared a spray composition. There are admixed 0.1 gm. cetyl-N-betaine, 0.1 gm. coco-N,N-dimethylamine oxide, 10 gms. isopropanol, and 0.02 gm. of citric acid. The mixture is heated to 40° C, cooled, and admixed with 100 gms. of liquified butane in a suitable container.

Resultant composition is sprayed under the armpits of several panelists. Each reports underarm odor control for at least 48 hours after use.

EXAMPLE 11

There are added to a suitable mixing vessel with stirring 8 gms. of coco-N-betaine, 8 gms. of stearyl-N-betaine, 16 gms. of 70/30 myristyl/palmitic-N,N-dimethylamine oxide, 3.3 gms. of citric acid and q.s. to 250 gms. of water. Resultant mixture is stirred vigorously and heated to 60° C for 15 minutes. Upon cooling, the pH of the mixture is found to possess a pH equal to 4.7.

Resultant composition is employed as a body wash following the procedure of Example 2 above. After 12 hours, it is found by each of five panelists that no body odor is detected and a bacterial count of 190 colonies per square inch is obtained. After 36 hours, no body odor is reported and the bacterial count rose to 600 colonies per square inch. The controls, however, in 24 hours all reported detectable body odor and bacterial colonies too numerous to count, when each of the controls constituting five panelists employs a modified composition of this example in which citric acid is omitted. The pH of the latter composition is 7.4.

EXAMPLE 12

This example illustrates the effect of using a typical composition of the invention on infected wounds.

Ten shaved Guinea pigs are incised. Two incisions are effected in each animal. These are approximately four centimeters in length. The two incisions are located on each animal parallel to the vertebral column, and extend through the dermal layer to the fascia. Each of the wounds is next innoculated with 0.1 milliliter of an 18 hour broth containing $10^8$ Staphylococcus aureus per milliliter. To one of the so innoculated wounds on each animal is added 0.1 ml. of the composition of Example 8 as a 13% solution and to the other wound is added 0.1 ml of an isotonic saline solution as a control. The wounds are then bandaged.

After 48 hours, the bandages are removed and the wounds are examined. They are swabbed for a culture of the remaining Staphylococcus aureus microorganisims.

It is observed that all the wounds treated with the composition of Example 8 had closed and were healing absent any substantial erythema or reddening. Further, eight of the ten wounds showed negative cultures. Of the wounds treated with the control composition (i.e., the isotonic saline solution) seven of the ten wounds remain open, four of the latter ten show bleeding on palpation, and all saline treated wounds show positive cultures of Staphylococcus aureus on swabbing and culturing.

EXAMPLE 13

This example illustrates the effect of a typical composition in treating a systemic infection caused by burns.

Following the procedure outlined by Stieritz et al in the Journal of Infectious Diseases, Vol. 131, No. 6 (June 1975), twenty female CFl mice (Carwroth Farms, Wilminton, Mass.) are shaved and anesthesized. Each is subjected to a non-lethal burn over 20% of the body surface for eight seconds and exposed to 0.2 ml of Pseudomonas aeruginosa M-2 at a concentration of $10^4$/ml.

Ten burned, infected mice are untreated and are taken as the controls. They are observed for fourteen days. Three of the ten mice died by day seven and are necropsied. Each shows positive cultures in the heart, spleen, and liver for the test organism.

Ten burned, infected mice are treated ten minutes after receiving the burn with 0.1 ml of the composition of Example 8 in a spray form employing "Freon" as the propellant. The burned, infected mice which are so treated are also observed for 14 days. However, none of the animals succumbed and show no signs of infection. The wounds healed normally.

EXAMPLE 14

This example illustrates the in vitro effect on a variety of microorganisms employing the composition of Example 8, above.

The microorganisms set forth in the table below are incubated for 24 hours and diluted with an isotonic saline solution to obtain a standard suspension of $10^8$ organisms per milliter.

The composition of Example 8 (i.e., germicide) is diluted with distilled water in 10 milliliter tubes to contain concentrations from 1.3 micrograms per milliliter to 130,000 micrograms per milliliter. Thereafter, 0.1 ml of the standard suspension of the organisms is innoculated into the various dilutions of the diluted germicide, stirred, and after 1,5, and 15 minute exposures are streaked on Letheen agar plates. As the Letheen ("Tween" 80-lecithin agar) inactivates the germicide, the lack of growth of the microorganisms on the streaked plates evidences germicidal activity of the test solutions. Each of the streaked plates is incubated for 48 hours at 35° C and examined for evidence of surviving organisms.

As indicated in Table III below, the numbers indicate the concentration expressed in micrograms per milliliter at which there is a complete absence of organisms, indicating total effectiveness of the combined components or germicide, namely, 100% kill. Each of the numbers ranging from 1.3 to 13,000 is termed the minimum cidal concentration in micrograms/ml.

The test solutions are controlled by omitting the germicide while innoculating the microorganisms into distilled water and plating the resultant solution onto Letheen agar. In all instances there is noted positive growth of 4+, i.e., the colonies are too numerous to count.

Table III

| Microorganism | Minimum Cidal Concentration in micrograms/ml. After exposure in minutes | | |
|---|---|---|---|
| | 1 min. | 5 min. | 15 min. |
| E. coli | 13 | 13 | 13 |
| K. pneumoniae | 130 | 13 | 13 |
| Salmonella typhimirium | 130 | 13 | 13 |
| Shigella sonnie | 13 | 1.3 | 1.3 |
| P. mirabilis | 1300 | 130 | 130 |
| Serratia maracens | — | 13000 | 130 |
| Mima polymorpha | 13 | 13 | 1.3 |
| Heilla vaginicola | 130 | 130 | 130 |
| Pseud. aeruginosa | 130 | 130 | 13 |
| Staph. aureus | 13 | 13 | 13 |
| Staph. epidermidis | 130 | 13 | 13 |
| β-Strep. | 130 | 130 | 13 |
| Strep. viridans | 130 | 130 | 130 |
| B. subtilis | 1300 | 1300 | 1300 |
| Candida albicans | 13 | 13 | 13 |

Similar results are noted when employing the composition of Example 3, above.

EXAMPLE 15

Following the procedure of Example 14 in every detail except that cetyl betaine, 70/30 myristyl/palmitic-N,N-dimethylamine oxide mixture, and a mixture of approximately 50/50 cetyl betaine and amine oxide are employed individually in lieu of the composition of Example 8. Each of the components or mixture is adjusted to a pH of 5.4 with citric acid. The microorganism selected is Staphylococcus aureus.

It is found that the minimum cidal concentration in micrograms/ml. for the betaine alone is 50, for the amine oxide it is 500 and for the mixture of the betaine and amine oxide, it is 5. This indicates that, in vitro, the mixture of components of the present invention exhibits at least a ten fold decrease in minimum cidal concentration as contrasted to the utilization of each of the components of the mixture.

EXAMPLE 16

The procedure of Example 14 is repeated in every detail except that cocobetaine, cocoamido-N,N-dimethylamine oxide and a mixture of approximately 50/50 cocobetaine and cocoamido-N,N-dimethylamine oxide are utilized individually in lieu of the composition of Example 8, above. Each of the components and the mixture is adjusted to a pH of 5.4 with citric acid and the microorganism selected is E.coli.

In this in vitro test, it is found that the minimum cidal concentration of micrograms per milliliter for the betaine is 50, for the amine oxide it is more than 5000, for the mixture of the two it is 5. Clearly, there is indicated for the mixture of components of the present invention at least a ten fold decrease against a gram negative organism in the minimum cidal concentration as contrasted to each of the individual components of the mixture.

I claim:

1. A broad spectrum, antimicrobial composition having low toxicity which consists of:
  (a) from 0.1 to 40 parts, by weight, of a higher alkyl-N-betaine, said betaine having the structure:

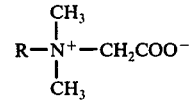

where R is a higher alkyl of from 10 to 18 carbon atoms, or mixed alkyl of the same,
  (b) from 0.1 to 40 parts, by weight, of a higher alkyl-N,N-dimethylamine oxide, a higher alkyl-N,N-dihydroxyethylamine oxide, or an acylamido t-amine oxide having the respective structure:

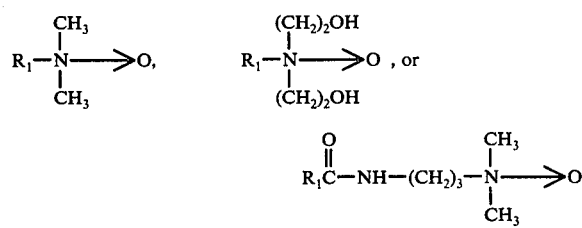

where $R_1$ is a higher alkyl of from 10 to 18 carbon atoms, or mixed alkyl of the same, and
  (c) a protonating agent, sufficient to adjust the pH of said composition from 4.0 to 5.5.

2. The composition of claim 1, wherein from 1 to 20 parts of each of said betaine and amine oxide are present.

3. The composition according to claim 1, wherein the alkyl-N-betaine is coco-N-betaine.

4. The composition according to claim 1, wherein the alkyl-N-betaine is stearyl-N-betaine.

5. The composition according to claim 1, wherein the higher alkylamine oxide is stearyl-N,N-dimethylamine oxide.

6. The composition according to claim 1, wherein the higher alkylamine oxide is myristyl/palmitic-N,N-dimethylamine oxide.

7. The composition according to claim 1, wherein the higher alkylamine oxide is coco-N,N-dimethylamine oxide.

8. The composition according to claim 1, wherein the higher alkylamine oxide is stearyl-N,N-dihydroxyethylamine oxide.

9. The composition according to claim 1, wherein the protonating agent is citric acid.

10. The composition according to claim 1, wherein the protonating agent is acetic acid.

11. The composition according to claim 1, wherein the said composition is in an aqueous medium and the pH thereof is adjusted to and maintained at from about 4.7 to about 5.2.

12. A method for inhibiting the growth of microorganisms selected from the class consisting of bacteria, fungi and protozoa which comprises: applying thereto an antimicrobially effective amount of the composition of claim 1.

13. The method according to claim 12, wherein the microorganisms are bacteria.

14. The method according to claim 12, wherein the growth of microorganisms are inhibited in incised wounds.

15. The method according to claim 12, wherein the growth of microorganisms are inhibited in pyogenic wounds.

16. The method according to claim 12, wherein the antimicrobially effective amount is defined as containing from 1 to 20 parts, by weight, of said composition.

* * * * *